US009733252B2

(12) United States Patent
Lowe (10) Patent No.: US 9,733,252 B2
(45) Date of Patent: Aug. 15, 2017

(54) METHODS AND SYSTEMS FOR LONG DISTANCE TAGGING, TRACKING, AND LOCATING USING WAVELENGTH UPCONVERSION

(71) Applicant: SRC, Inc., North Syracuse, NY (US)

(72) Inventor: Adam J. Lowe, Syracuse, NY (US)

(73) Assignee: SRC, INC., North Syracuse, NY (US)

( * ) Notice: Subject to any disclaimer, the term of this patent is extended or adjusted under 35 U.S.C. 154(b) by 0 days.

(21) Appl. No.: 13/749,287

(22) Filed: Jan. 24, 2013

(65) Prior Publication Data

US 2013/0190192 A1    Jul. 25, 2013

Related U.S. Application Data

(60) Provisional application No. 61/589,978, filed on Jan. 24, 2012.

(51) Int. Cl.
| | |
|---|---|
| G01N 33/58 | (2006.01) |
| C12Q 1/68 | (2006.01) |
| G02B 5/00 | (2006.01) |
| G01S 17/74 | (2006.01) |
| B82Y 15/00 | (2011.01) |
| B82Y 20/00 | (2011.01) |
| G01N 21/64 | (2006.01) |

(52) U.S. Cl.
CPC ......... G01N 33/582 (2013.01); C12Q 1/6825 (2013.01); G01S 17/74 (2013.01); G02B 5/008 (2013.01); B82Y 15/00 (2013.01); B82Y 20/00 (2013.01); G01N 21/648 (2013.01); G01N 21/6428 (2013.01); Y10S 977/742 (2013.01); Y10S 977/924 (2013.01)

(58) Field of Classification Search
None
See application file for complete search history.

(56) References Cited

U.S. PATENT DOCUMENTS

| 7,489,870 B2 | 2/2009 | Hillis et al. |
| 7,649,665 B2 | 1/2010 | Kempa et al. |
| 7,847,236 B2 | 12/2010 | Bratkovski et al. |
| 8,053,744 B2 | 11/2011 | Bortolin |

(Continued)

FOREIGN PATENT DOCUMENTS

| WO | WO2009150598 | * 12/2009 |
| WO | 2011136527 A2 | 3/2011 |
| WO | 2011050272 A2 | 4/2011 |

OTHER PUBLICATIONS

Calzaferri et al. Angew Chem Int Ed Engl. Aug. 18, 2003;42(32):3732-58.*

(Continued)

*Primary Examiner* — Betty Forman
(74) *Attorney, Agent, or Firm* — Bond Schoeneck & King, PLLC; George McGuire; Blaine Bettinger (57) ABSTRACT

Methods and systems for plasmonically enhanced bionanoantennas for tagging, tracking, and locating targets of interest at long distances in both day and nighttime conditions. The nanoantennas are used to tag a target of interest and emit a wavelength to impart a unique biometric signature. The nanoantennas are detectable by selectively harvesting and plasmonically enhancing incident light in the visible region, then upconverting that energy through an activated phosphor.

10 Claims, 7 Drawing Sheets

(56) References Cited

U.S. PATENT DOCUMENTS

| | | | |
|---|---|---|---|
| 2005/0260764 A1* | 11/2005 | Grigsby, Jr. | G01N 21/6428 436/172 |
| 2006/0210279 A1* | 9/2006 | Hillis et al. | 398/118 |
| 2007/0058686 A1 | 3/2007 | Capasso et al. | |
| 2008/0231445 A1 | 9/2008 | Rodgers | |
| 2008/0251723 A1 | 10/2008 | Ward et al. | |
| 2008/0299559 A1 | 12/2008 | Kwok et al. | |
| 2009/0140128 A1 | 6/2009 | Oldham et al. | |
| 2009/0153871 A1 | 6/2009 | Rosenthal et al. | |
| 2010/0103504 A1 | 4/2010 | Lawandy | |
| 2010/0258743 A1* | 10/2010 | Bortolin | G01N 21/643 250/461.2 |
| 2011/0170103 A1 | 7/2011 | Gomez Rivas et al. | |
| 2011/0249259 A1 | 10/2011 | Van Dorpe et al. | |
| 2011/0306141 A1 | 12/2011 | Bronchetti et al. | |
| 2013/0148194 A1* | 6/2013 | Altug et al. | 359/350 |

OTHER PUBLICATIONS

International Search Report Form PCT/ISA/220, International Application No. PCT/US2013/022911, pp. 1-11, Dated May 14, 2013.

Dragan et al. Indium nanodeposits: A substrate for metal-enhanced fluorescence in the ultraviolet spectral region. Journal of Applied Physics [Online] 2010, vol. 108, Issue 9, pp. 1-7.

Talley. Remotely Triggered Solar Blind Signaling Using Deep Ultraviolet (UV) LEDs. [Online] 2011, pp. 1-71. http://edocs.nps.edu/npspubs/scholarly/theses/2011/June/11Jun_Talley.pdf (accessed Feb. 2, 2012).

Zhang et al. Plasmonic Modulation of the Upconversion Fluorescence in NaYF4:Yb/Tm Hexaplate Nanocrystals Using Gold Nanoparticles or Nanoshells. Angewandte Chemie International Edition [Online] 2010, vol. 49, Issue 16, pp. 2865-2868.

* cited by examiner

METHODS AND SYSTEMS FOR LONG DISTANCE TAGGING, TRACKING, AND LOCATING USING WAVELENGTH UPCONVERSION

CROSS-REFERENCE TO RELATED APPLICATIONS

This application claims priority to U.S. Provisional Patent Application Ser. No. 61/589,978, filed on Jan. 24, 2012 and entitled "Long Distance Tagging, Tracking, and Locating by Plasmonically Enhanced Bionanoantennas," the entire disclosure of which is incorporated herein by reference.

BACKGROUND OF THE INVENTION

1. Field of the Invention

The present invention relates to optical tagging, tracking, and locating, and, more specifically, to optical tagging, tracking, and locating at significant distances.

2. Description of the Related Art

Long distance tagging, tracking, and locating ("TT&L") is a major challenge. Current TT&L capabilities most often use radio frequencies ("RF") to find their targets. This is becoming increasingly challenging in an RF jammed environment. Additionally, active RF emitters require a power source limiting their lifetime and range. Passive RF tags must be probed by an active source which can be readily detected and jammed. Current optical techniques are limited due to several problems. Most detection systems work in the visible or near-IR wavelengths. While this can have some advantages, such as near-IR's ability to cut through obscurants, it is very challenging to detect these wavelengths in daylight conditions due to the high background signal of ambient light. Significant polarization and grating of the light is required to detect any signal over the background. This process discards most of the emission signal and therefore has a very difficult time detecting signals at a significant distance.

The current optical emitters also suffer from inherent difficulties in the environment. Quantum dots, which have become quite popular, suffer from "blinking" as they get caught in their triplet state and electrons are unable to relax back down to the ground state. This makes pulsed detection and emission gating very difficult. UV-C quantum dots, which would at least solve the "solar-blind" problem, are also not available as no quantum dot has been synthesized to emit in the UV-C region. Organic fluorophores, which are an alternative to quantum dots, are susceptible to photobleaching and their optical performance is highly dependent on their local environment and solvation state. Finally, systems which simply functionalize quantum dots or fluorophore labeled particles do not emit the needed amount of light for long distance detection because of significant scattering effects. Light is not efficiently harvested and transferred to its emitting fluorophore, and particle composition and structure is not optimized to enhance photonic emission for detection. These combined optical inefficiencies make it extremely difficult if not impossible to perform optical tagging and tracking at significant distances.

Innovative technologies are therefore required for optical tagging, tracking, and locating at significant distances that avoid one or more problems currently faced by the state-of-the-art in TT&L capabilities.

BRIEF SUMMARY OF THE INVENTION

It is therefore a principal object and advantage of the present invention to provide a method, device, and/or system for improved optical tagging, tracking, and locating at significant distances.

It is another principal object and advantage of the present invention to provide a method, device, and/or system for improved optical tagging, tracking, and locating at significant distances using a nanoantenna array.

It is a further object and advantage of the present invention to provide a method, device, and/or system for improved optical tagging, tracking, and locating at significant distances, thereby resulting in a significant improvement in operation capabilities.

Other objects and advantages of the present invention will in part be obvious, and in part appear hereinafter.

According to a first aspect, a nucleic acid tag comprising: (i) an agglomerated plurality of nanoparticle nucleotide-support platforms each attached to a plurality of nucleic acid molecules, each of said nucleic acid molecules comprising identifying information, wherein a spacer is located between said nanoparticle nucleotide-support platform and said identifying information; (ii) an upconverting fluorescent material; and (iii) an encapsulant surrounding said agglomerated plurality of nanoparticle nucleotide-support platforms and said plurality of nucleic acid molecules, wherein when the nucleic acid tag is exposed to electromagnetic radiation of a first wavelength, the upconverting fluorescent material emits electromagnetic radiation of a second wavelength, said second wavelength being shorter than said first wavelength.

According to an aspect, the nucleic acid tag further comprises a plasmonic enhancer.

According to another aspect, the encapsulant is adapted to prevent degradation of the plurality of nucleic acid molecules.

According to one aspect, each of the plurality of nucleic acid molecules is composed of nucleotides selected from the group consisting of ribonucleotides, deoxyribonucleotides, and nucleotide analogues. The plurality of nucleic acid molecules can be one or more types of oligonucleotide, or can be genomic deoxyribonucleic acid ranging from two nucleotides to the entire genome. Further, information can be encrypted within the nucleic acid molecule by altering the sequence of nucleotides.

According to another aspect, a plasmonically enhanced nanoantenna comprising: (i) a plurality of nanochannels, wherein said nanochannels are adapted to receive electromagnetic radiation of a first wavelength; (ii) an upconverting fluorescent material in communication with said plurality of nanochannels, wherein when the nanoantenna is exposed to said electromagnetic radiation of said first wavelength, the upconverting fluorescent material emits electromagnetic radiation of a second wavelength, said second wavelength being shorter than said first wavelength.

According to an aspect, the plurality of nanochannels are etched on a substrate.

According to another aspect, the nanoantenna comprises a layer of a noble metal, such as silver, among many others.

According to an aspect, the fluorophore is bound to zeolite, and/or is bound to a nanotube.

According to another aspect, a method for detecting a nanoantenna in or on an item of interest, the method comprising: providing a nanoantenna, the nanoantenna comprising: (i) a plurality of nanochannels, said nanochannels adapted to receive electromagnetic radiation of a first wavelength; and (ii) an upconverting fluorescent material in communication with said plurality of nanochannels, wherein when the nanoantenna is exposed to said electromagnetic radiation of said first wavelength, the upconverting fluorescent material emits electromagnetic radiation of a second wavelength, said second wavelength being shorter than said first wavelength; adding the nanoantenna to the item of interest; irradiating, from a remote location, electromagnetic radiation at said first wavelength onto at least a portion of the item of interest; and monitoring the item of interest for emission of electromagnetic radiation at said second wavelength; wherein detection of electromagnetic radiation emitted at said second wavelength indicates the presence of the nanoantenna.

According to an aspect, the presence of the nucleic acid tag authenticates the item of interest.

According to another aspect, the nanoantenna comprises a layer of a noble metal, such as silver, among many others.

According to an aspect, the fluorophore is bound to zeolite, and/or is bound to a nanotube.

According to a further aspect, a plurality of nucleic acid molecules are attached to said nanoantenna. The nucleic acid molecules can be composed of nucleotides selected from the group consisting of ribonucleotides, deoxyribonucleotides, and nucleotide analogues. Further, information can be encrypted within at least one of the plurality of nucleic acid molecules.

According to another aspect, a method for determining whether an item has moved through a geographic location using a nanoantenna, the method comprising: providing a nanoantenna, the nanoantenna comprising: (i) a plurality of nanochannels, said nanochannels adapted to receive electromagnetic radiation of a first wavelength; and (ii) an upconverting fluorescent material in communication with said plurality of nanochannels, wherein when the nanoantenna is exposed to said electromagnetic radiation of said first wavelength, the upconverting fluorescent material emits electromagnetic radiation of a second wavelength, said second wavelength being shorter than said first wavelength; seeding the geographic location with the nanoantenna; and examining the item for the presence of the nanoantenna.

According to an aspect, each geographic location is seeded with a unique nanoantenna.

According to another aspect, a plurality of nucleic acid molecules are attached to said nanoantenna. The nucleic acid molecules can be composed of nucleotides selected from the group consisting of ribonucleotides, deoxyribonucleotides, and nucleotide analogues. Further, information can be encrypted within at least one of the plurality of nucleic acid molecules.

According to an aspect, the method further comprises the step of analyzing at least a portion of the sequence of at least one of said plurality of nucleic acid molecules.

According to another aspect, a method for backtracking the travel history of an item, the method comprising: providing a first nanoantenna, the first nanoantenna comprising: (i) a plurality of nanochannels, said nanochannels adapted to receive electromagnetic radiation of a first wavelength; and (ii) a first upconverting fluorescent material in communication with said plurality of nanochannels, wherein when the first nanoantenna is exposed to said electromagnetic radiation of said first wavelength, the first upconverting fluorescent material emits electromagnetic radiation of a second wavelength, said second wavelength being shorter than said first wavelength; providing a second nanoantenna, the second nanoantenna comprising: (i) a plurality of nanochannels, said nanochannels adapted to receive electromagnetic radiation of a third wavelength; and (ii) a second upconverting fluorescent material in communication with said plurality of nanochannels, wherein when the second nanoantenna is exposed to said electromagnetic radiation of said first wavelength, the second upconverting fluorescent material emits electromagnetic radiation of a fourth wavelength, said fourth wavelength being shorter than said third wavelength; seeding each of two or more geographic locations with said nanoantennas, wherein each geographic location is seeded with a unique nanoantenna; examining said item for the presence of one or more nanoantennas; and identifying the geographic location associated with each nanoantenna detected on said item.

According to an aspect, the first wavelength and said third wavelength are the same.

According to a further aspect, the method further comprises the step of extrapolating the point of origin of said item.

According to another aspect, a method for backtracking the travel history of an item, the method comprising: providing a plurality of nanoantennas, each nanoantenna comprising: (i) a plurality of nanochannels, said nanochannels adapted to receive electromagnetic radiation of a first wavelength; (ii) an upconverting fluorescent material in communication with said plurality of nanochannels, wherein when the nanoantenna is exposed to said electromagnetic radiation of said first wavelength, the upconverting fluorescent material emits electromagnetic radiation of a second wavelength, said second wavelength being shorter than said first wavelength, and further wherein a plurality of nucleic acid molecules comprising a first nucleic acid sequence are attached to a first subset of said plurality of nanoantennas, and further wherein a plurality of nucleic acid molecules comprising a second nucleic acid sequence are attached to a second subset of said plurality of nanoantennas; seeding at least two or more geographic locations with said nanoantennas, wherein the first geographic location is seeded with said first subset of nanoantennas, and the second geographic location is seeded with said second subset of nanoantennas; examining said item for the presence of one or more nanoantennas; and identifying the geographic location associated with each nanoantenna detected on said item.

According to a further aspect, information is encrypted within at least one of said nucleic acid molecules.

According to another aspect, the method further comprises the step of analyzing at least a portion of the sequence of at least one of said nucleic acid molecules.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
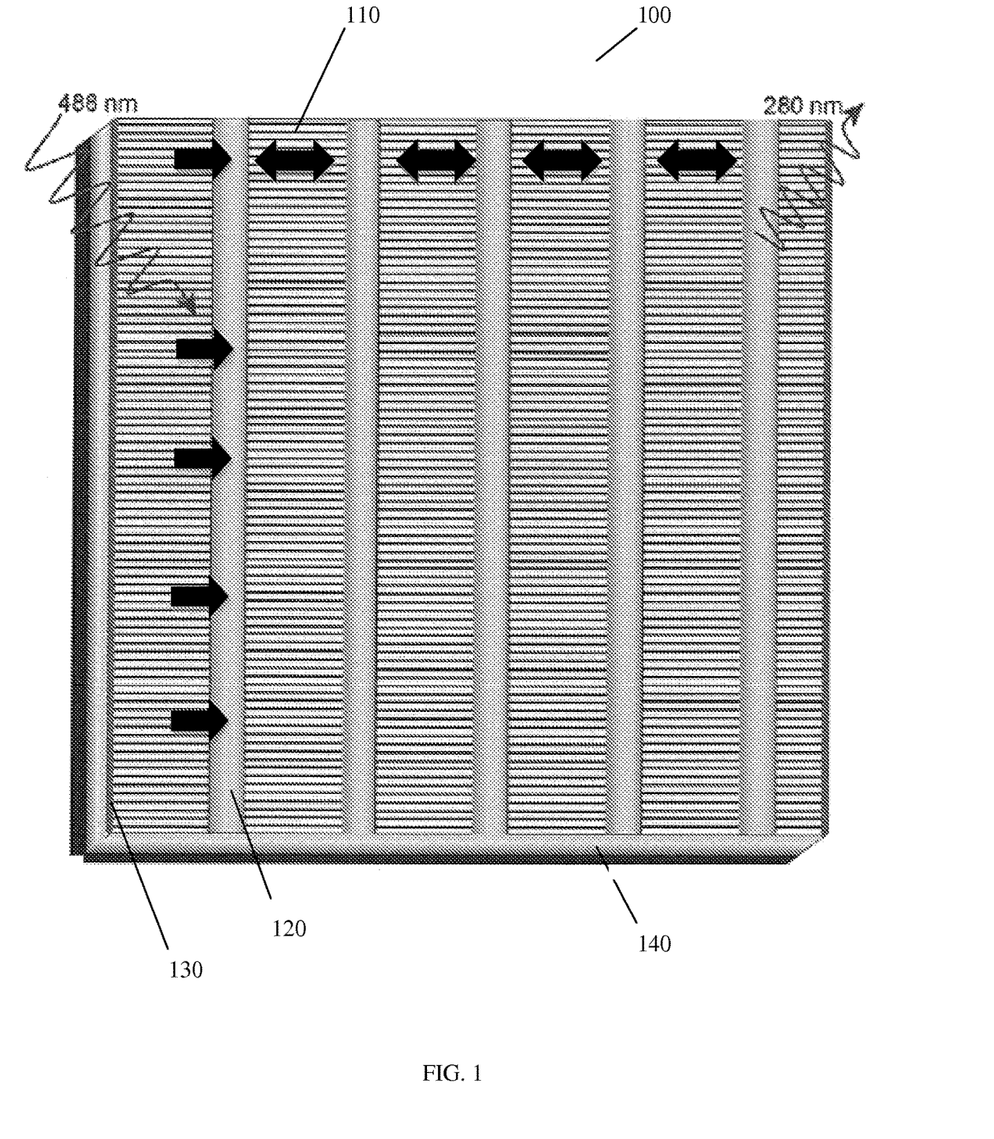
FIG. 1 is a schematic of a nanoantenna according to one embodiment.
Figure 2:
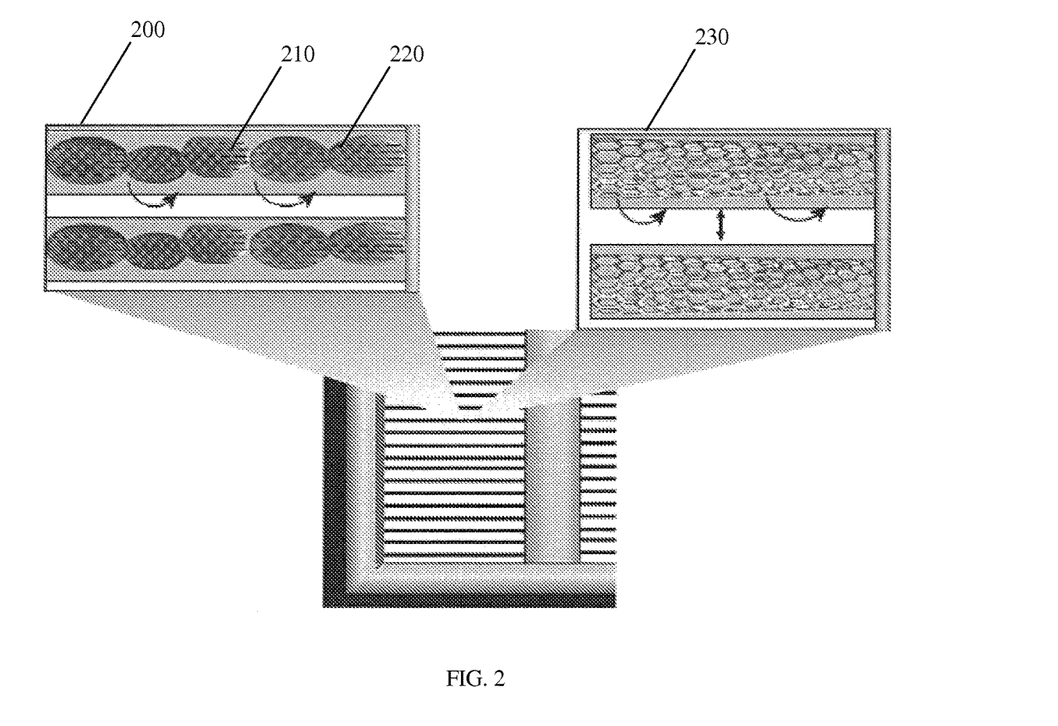
FIG. 2 is a schematic of optical wiring of a nanoantenna according to one embodiment.

Referring now to the drawings wherein like reference numerals designate identical or corresponding parts throughout the several views, there is shown in FIG. 1 a schematic of a plasmonically enhanced bionanoantenna. According to an embodiment, the bionanoantenna 100 comprises arrayed nanochannels on a nanoparticle (micron-sized 1-1000 um, for example) to capture an excitation wavelength of light, and then transfers that energy via FRET to an emitting phosphor which can upconvert the light to UV-C. According to the embodiment depicted in FIG. 1, bionanoantenna 100 comprises optical wiring 110 that receives incident light, and that energy is coupled into the UV-C emitting phosphor 120. Optionally, the bionanoantenna comprises one or more optical 'plugs' 130 to direct unidirectional energy movement. Energy flow in FIG. 1 is represented in part by the arrows. According to one embodiment, bionanoantenna 100 comprises a nanothin layer of colloidal silver 140 which, for example, can help trap incident light energy and enhance UV-C fluorescence from the emitter.

The conversion to UV-C solves numerous spectral detection problems. For example, the arrayed nanochannels can comprise fluorophores which can capture light and have very limited molecular movement, making the FRET efficient. The fluorophores can be bound to, for example, zeolite crystals and/or nanotubes to act as conductors, although other configurations are possible depending upon the design of the system and the needs of the designers and/or users. Other carries which restrict the molecular movement of the light acceptor are also possible. The coupling effect is further enhanced by the use of a silver base layer 140 or other noble metal (including but not limited to ruthenium, rhodium, palladium, osmium, iridium, platinum, and gold) to act as a plasmon conductor and to achieve metal enhanced fluorescence. In one embodiment, described herein, the nanoparticle base is functionalized with DNA or other material in order to stick to a target.

In one embodiment, the methods, systems, and devices described herein investigate the ability to clandestinely tag and track targets of interest at long distances in both day and nighttime conditions. This can be achieved by monitoring the UV-C wavelength emissions from novel, plasmonically enhanced bionanoantennas ("BNAs") tagging the target. The tags will stick to the target through strong electrostatic interactions due to their size and functionalization (optionally DNA, for example, although many other methods of functionalization are possible), which also imparts a unique biometric signature. The BNAs will be detectable by selectively harvesting and plasmonically enhancing incident light in the visible region, then upconverting that energy into the UV-C "solar-blind" region through an activated phosphor. This "solar blind region" is detectable in both daytime and nighttime conditions due to almost complete atmospheric absorbance of solar radiation at this wavelength. This upconverted UV-C light can then be detected from a stand-off sensor as depicted, for example, as an embodiment in FIG. 3, although many other detection devices and methods are possible.

It should be noted that while many of the embodiments described herein harvest and/or employ an excitation wavelength in the visible region, the excitation wavelength could be a number of other possible regions, including but not limited to short-wavelength infrared, near-infrared, or other wavelengths. Any wavelength that can be harvested and used for upconversion would be suitable.

This approach is innovative because it solves, for example, the "solar-blind" optics problem, efficiently harvests and enhances light due to its unique architecture, and can function in a challenging RF environment. Additionally, microcube shaped particles can strongly bind their target due to their size and optional DNA functionalization.

As seen in FIG. 2, showing a zoomed view of optical wiring, the system can harvest light in the visible region from an excitation source then focus that light to emitting elements, using, for example, dye doped zeolite crystals or carbon nanotubes as optical wiring (in addition to other designs and configurations). For example, in frame 200 of FIG. 2, nanochannels 210 (shown as black lines) within the crystal can be seen with light harvesting molecules 220 (shown as black dots). Optionally, optical wiring uses functionalized carbon nanoparticles, as shown in frame 230. In both frames, energy transfer along and between the tubes is shown, and silver plasmonic enhancer is also depicted. An activated phosphor emitting element then upconverts the light to the UV-C region through an anti-stokes mechanism. This upconversion to the UV-C region is beneficial as there is no background light in the region because it is all absorbed by the atmosphere. This can impart on the system a very high signal to noise ratio.

Examples of upconverting materials include crystals or glasses doped with ions of rare earth metals, such as ytterbium (Yb) or thulium (Tm). The energy level of the emitted photons and the wavelength of the light emitted from the upconverting materials is uniquely characteristic of the particular upconverting material used. Anti-stokes upconverters are known in the art, and can include, but are not limited to, components including one or more various lanthanides, actinides, and transition metals, including Pr, Nd, Gd, Dy, Ho, Er, Tm, U, and Am, among many others. An anti-stokes upconverter can be an ion-doped crystal, doped with one or more of the ions described above or known in the art. For example, $LaCl_3:U^{3+}$, $NaYF_4:Yb^{3+}$, and $Y_2BaZnO_5$ or $Gd_2BaZnO_5$ doped with lanthanide ions such as $Yb^{3+}$, $Er^{3+}$, $Ho^{3+}$ and $Tm^{3+}$, and just a few examples of ion-doped crystals that can be used as upconverters. Many others are known in the art.

According to one embodiment, light is not transferred along the optical wire, just the energy from the incident light. The energy is transferred from molecule to molecule through Forster enhanced resonance energy transfer ("FRET"). Energy transfer via FRET is efficient in this embodiment of the system because of the nanochannels in the zeolite microcrystals and the intrinsic properties of single wall carbon nanotubes, as seen in FIG. 2. The nanochannels within the zeolite microcrystal control the packing and interaction between the molecules. By optimally spacing and orienting the conducting molecules, efficient interaction and conduction of the energy can take place. Carbon nanotubes can act as optical wires due to their ability to conduct energy along their transverse axis as well as couple energy between the nanotubes. Their ability to harvest light can be greatly enhanced by conjugating a light harvesting molecule similar to those in the zeolite nanochannels.

Both carbon nanotubes and zeolite can serve as optical conduits to the emitting phosphor because of their different optical properties and mechanisms of energy transport. As seen in FIG. 2, the conduction of light energy can be further enhanced by applying a plasmonically active coating of colloidal silver below the optical wiring elements. This ultrathin coating of silver acts as a further conduit of energy as electrons can couple through its plasmonic field, into the emitting element. Colloidal silver also absorbs light at the excitation wavelength and can harvest light missed or scattered by the optical wiring elements into the emitting element. The upconverting, inorganic phosphor emitting element can also be made more efficient by utilizing the metal enhanced fluorescence phenomena. When fluorescing compounds are within a few angstroms of some metals, they are quenched through electron transfer. However, when they are slightly farther away, their fluorescence is actually greatly enhanced. This is due to the "lightening rod" effect of the particles which increases the rate of excitation, and also the effect of increased rate of emission (electron turn-over). This should significantly help the emission of the upconverted UV-C wavelength, as it will have a relatively low quantum yield prior to metal enhanced fluorescence.

Although using visible light as the excitation wavelength might be easier and safer in some circumstances, a 244 nm excitation source can be used to excite the phosphor to produce the desired 280 nm "solar blind" emission peak. This would eliminate the upconversion step and will be considered if the desired quantum efficiency cannot be achieved with visible light as the excitation source. Overall, this precisely designed system will harvest and emit much more light than current technologies and will be useful in day or night operations.

Example 1

Nanoantenna Manufacture

According to one embodiment is an exemplary process for creating a suitable nanoantenna in accordance with one embodiment. As an initial step, a nanoantenna array is constructed on an Si wafer. For example, the Si wafer can be a traditional four-inch wafer. Alternatively, the wafer can be any other suitable material. This allows the demonstration of the optical capabilities of the system while eliminating technical challenges associated with producing the system in particle format. E-beam lithography and metal vapor deposition techniques are used to achieve the array features described above. According to another embodiment, individual nanoparticles are produced.

One aspect of this design is to optimally align the "optical wire" molecules in the zeolite nanocrystal and to align the carbon nanotubes. Optical wire alignment in the zeolite crystals is achieved, for example, based upon previous literature, molecular orbital modeling, and empirical testing of carrier molecule types and concentrations. Carbon nanotube alignment and packing density is achieved, for example, by the "surface flow" technique which allows carbon nanotubes to be oriented in a channel by liquid deposition using a PDMS mask.

Additionally, many other methods and systems for nanoantenna array manufacture, creation, and testing are possible.

Example 2

Optical Testing

Figure 3:
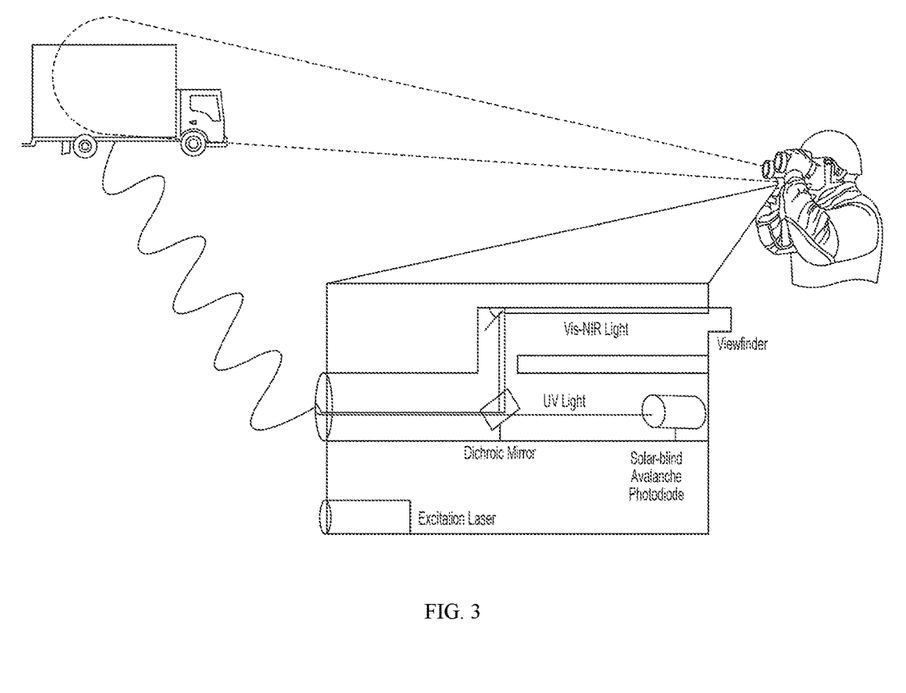
FIG. 3 is a schematic of a nanoantenna detection device and use according to one embodiment.

Optical testing is achieved, for example, by using a 488 nm laser as the excitation source with a separate optical detection system. The detection array consists, for example, of a modified, large diameter commercial telescope coupled to a solar-blind avalanche photodiode, similar to the final technology envisioned in FIG. 3. According to one embodiment, a large diameter telescope will enable collection of more scattered light from the taggant array, especially at significant distances. In order to simulate the random facing of particles, the experimental wafers cam be excited over a range of angles with respect to the excitation source. The intensities can be averaged to give a reasonable estimation of a well labeled spot on a target. UV-C emissions will be detected over a range of distances. It is anticipated that maximum detection distance will improve as the project progresses through improvement of the BNA array chemistry and architecture.

Additionally, many other methods and systems for nanoantenna testing and detection are possible, including other methods and systems described herein.

Example 3

DNA Functionalization

Figure 4:
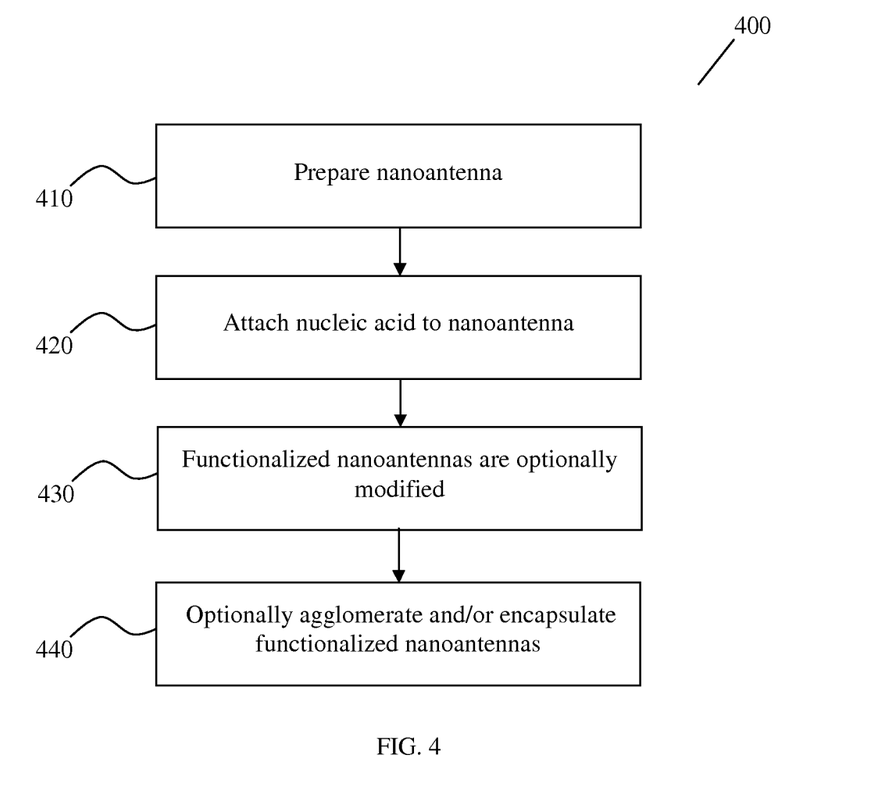
FIG. 4 is a flowchart of a process for creating a nanoantenna in accordance with an embodiment.

According to one embodiment, the nanoantenna is functionalized with nucleic acid to enhance tagging or sticking to target objects. For example, shown in FIG. 4 is an exemplary process for creating a nucleic acid functionalized nanoantenna. At step 410, the nanoantenna is prepared using, for example, one of the methods described above. The nanoantenna can be optionally prepared for downstream functionalization using any of a number of known methods. One such method could comprise, for example, an additional blocking step that prevents the nanoantenna from become completely covered by nucleic acid, thereby preventing energy absorption and/or detection.

At step 420, the nucleic acid molecule is attached to the nanoantenna. The nucleic acid can be any natural or artificial nucleic acid, including but not limited to deoxyribonucleotides, ribonucleotides, oligonucleotides, nucleic acid analogs, and similar molecules that are either artificial or are otherwise found in nature, as well as combinations of any or all of the above. The nucleic acids can range from a very short sequence to a complete genome, for example. In one embodiment, a chemical linker is used to connect the nucleic acid to the nanoantenna. This chemical linker must keep the nucleic acid securely tethered to the nanoantenna while avoiding inhibition of the detection or analysis of the nanoantenna and/or nucleic acid. Although the chemical linker can be chosen to provide a permanent covalent link between the nucleic acid and the nanoantenna, it could also be a compound that quickly and efficiently releases the nucleic acid at a certain temperature or after exposure to a release compound.

The nucleic acid molecule can also be designed to promote analysis. For example, to avoid steric hindrance or unwanted intermolecular interactions, the molecule can include nucleotide spacers between the chemical linker or nanoantenna and any information-coding segment of the nucleotide sequence.

The concentration of nucleic acid molecules on the nanoantenna is also an important factor in downstream analysis. If the molecules are too concentrated, the nanoantenna will be unable to receive or emit energy at any wavelength.

According to another embodiment, the nucleic acid molecules are attached to the nanoantenna by synthesizing the nucleic acid directly onto the nanoantenna. There are a variety of methods for performing this step.

At step 430, which can occur at the position shown in the flowchart or before or after any other step after derivatization of the nanoantennas, the derivatized nanoantennas can optionally be modified for any purpose, use, or design. For example, a flame or fire retardant can be added to the derivatized nanoantennas. The flame or fire retardant is preferably anything known by those skilled in the art to inhibit combustion or reduce the temperature of associated material in response to high temperatures, including but not limited to Nomex®, GORE-TEX®, Kevlar®, aluminum hydroxide, magnesium hydroxide, hydromagnesite, calcium silicate, or halocarbons, among many others. While some compounds provide the nanoantenna with resistance to combustion, others provide the nanoantenna with thermal protection by absorbing heat in an endothermic reaction, through chemical degradation, or by otherwise protecting the tag from high temperatures.

At step 440 of the exemplary method, the functionalized nanoantennas are optionally agglomerated. Agglomeration may protect the nanoantenna from degradation and/or facilitate encapsulation. The functionalized nanoantennas can also optionally be encapsulated, which may protects the nanoantennas from degradation by hydrolysis, enzymatic digestions, chemical degradation, or any other means. Additionally, the encapsulant should enhance the ability of the tag to discretely attach to people and objects. If covertness is required, the encapsulant can be designed to deter detection. The encapsulating layer can also be designed with surface moieties added to the inner or outer surfaces of the encapsulant or incorporated into the encapsulant material. The moieties are designed to facilitate a particular use of the nanoantennas. For example, the moiety can be hydrophobic to enable stickiness or contain antibodies designed for specific targeting. The molecular interactions between the moiety and a target compound can range from simple electrostatic interactions to antibody-antigen recognition. The moiety can also promote detection of the nanoantennas.

Example 4

Tagging, Tracking, and Locating Using Nanoantennas

The methods, systems, and devices described herein result in technology that can be applied to a variety of TT&L applications, such as target and material tracking, event backtracking operations, and even tamper detection. It will enable day and night TT&L operations at a significant distance, which could provide the intelligence community a significant advantage. In addition to the significant optical capabilities of the tag, the unique DNA signature provides a powerful identification mechanism. By physically sampling the target and running a quantitative PCR test in the field, an operator can determine the unique DNA sequence, which can correlate to critical information such as deployment date or area and cross reference this with a target database.

Indeed, once the nanoantenna is created it can be used for numerous unique security applications including to: (i) detect illicit tampering with physical objects; (ii) secure the privacy of a room or building; (iii) send encoded messages between individuals; (iv) detect a tagged individual or object at a distance; (v) track the recent travel history of an individual or object; or (vi) monitor a location of interest, among many other uses.

Figure 5:
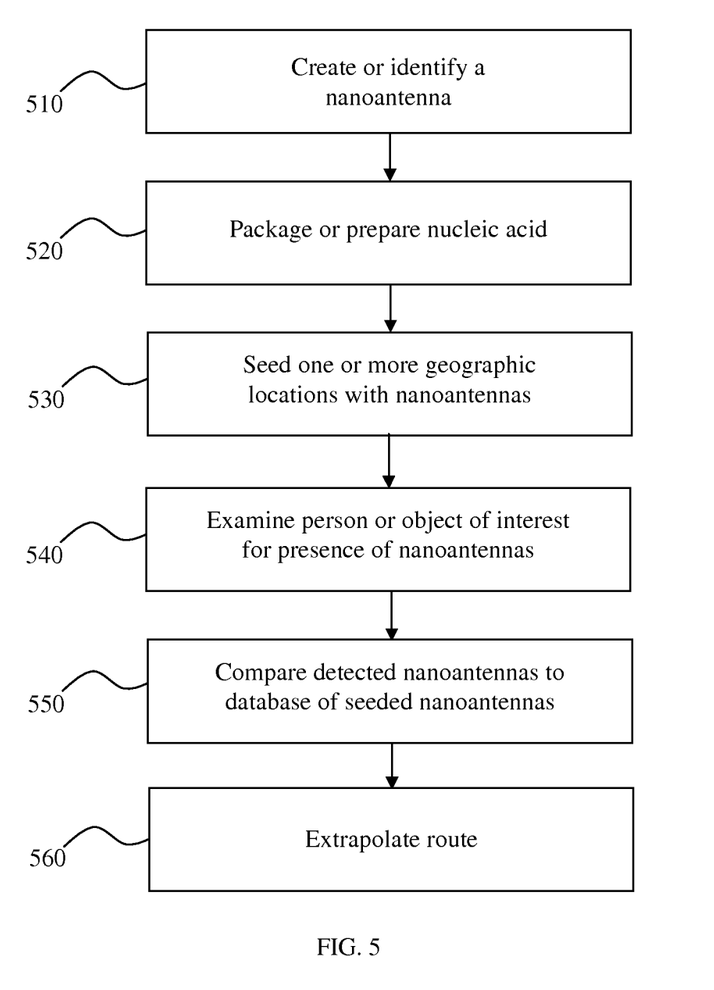
FIG. 5 is a flowchart of a process for using a nanoantenna in accordance with an embodiment.

FIG. 5 is a schematic representation of an embodiment of a security method according to the present invention. More specifically, the figure represents characterization of the recent travel history of point of an item. An item can be any person or object of interest. Seeding an area with nanoantennas that naturally or artificially adhere to objects (including people or animals) provides a mechanism for identifying the origin of those objects simply by identifying and/or analyzing the adhering nanoantenna. Similarly, by seeding different areas with discernibly different nanoantennas it is possible to backtrack the geographic path that an object has followed. Such a mechanism would allow the seeder—the person or organization who seeded and will analyze the tags—to identify the recent travel history of the person or object; to quickly identify people or objects that have traveled through seeded areas; and to identify vehicles that have traveled through seeded areas and might carry dangerous cargo such as explosives, among other uses.

As an initial step 510, a suitable nanoantenna is characterized or created. In step 520 of the exemplary method shown in FIG. 5, the nanoantenna is packaged, prepared, or otherwise modified prior to use. Preparation of the nanoantenna can range from little or no preparation or modification to an extensive series of steps for modifying the nanoantenna. For example, the nanoantenna can be functionalized with nucleic acid, as described above, or can be added to another structure or base.

According to one embodiment, the nucleic acid molecules can contain primer-binding sequences surrounding unique nucleotide sequences. The unique nucleotide sequence contained between the primers can encode information that corresponds to an identification, location, date, time, or other data specific to that unique sequence. Since analysis of every nucleic acid molecule can use the same primers, the analysis can be performed faster and more efficiently. The primer sequences, whether they are unique or identical for each location or use, are chosen to avoid cross-reactions with naturally-occurring nucleic acid molecules in the environment in which the nucleic acid is located. Although only a fraction of natural nucleic acid molecules on Earth have been characterized by scientists, the search of nucleic acid repository databases such as GenBank®, the National Institutes of Health database containing all publicly available DNA sequences, could be a preliminary step in constructing the primer sequences.

In one embodiment of the current invention, unique groupings of nucleotides are assigned a specific letter, number, or symbol value in order to encode information within the sequence. By placing the unique groupings in order, information can be encrypted into the nucleotide sequence. To further increase the security of the information, advanced encryption algorithms can be used to assign letter, number, or symbol values to specific nucleotides or nucleotide groupings. Additionally, the encryption system can be periodically changed to prevent decryption by intercepting entities.

The nucleic acid can also be encoded to contain information other than a string of letters, numbers, and symbols. For instance, the sequence can be a random sequence that corresponds to the item, location, or date that the object of interest will be seeded. Alternatively, the tag can be as simple as a single nucleic acid change in a previously identified or known sequence. For example, the nucleotide sequence can be embedded in a full or partial genomic sequence corresponding to an organism which naturally exists in the location to be seeded. Modifications to the natural nucleic acid sequence, known only to the creator of the tag, can be made such that the changes resemble natural variations of the sequence and thus fail to arouse suspicion, even by individuals that might suspect such tags are present.

To decrypt the encoded information according to this system, an individual will need: (1) knowledge that encoded nucleic acid is present; (2) knowledge of the specific location of the information within the nucleic acid in order to use the appropriate primers for amplification and sequencing reactions; (3) access to a PCR machine and reagents; and (4) the encryption algorithm, or, alternatively, complex decryption capabilities.

Although creating the nucleic acid target within the genome of a naturally-occurring organism provides numerous benefits, both in vivo and in vitro DNA replication occasionally introduces random errors into a DNA sequence despite the actions of proof-reading and repair enzymes. By deleting one or more nucleotides or frame-shifting the nucleic acid sequence, these mutations can disrupt any encrypted information contained therein. Computer algorithms are used to restore the information by recognizing and repairing the errors. For example, if a mutation adds one or more nucleotides to a pre-defined sequence and disrupts the information, the algorithm removes single or multiple nucleotides from the sequence until the information is corrected. Similarly, if a mutation removes one or more nucleotides, the algorithm systematically adds nucleotides to the sequence until the information is corrected. The algorithm must also be robust enough to decrypt sequences that contain more than one type of error-inducing mutation, and must be capable of recognizing when the information contained with the nucleic acid has been restored.

At step 530 of the exemplary method depicted in FIG. 5, one or more geographic locations are seeded with the nanoantennas. The locations are seeded with nanoantennas using any mechanism that will adequately disperse the nanoantennas at the desired concentration. For example, the nanoantennas can be seeded on and along roadways or paths using an automobile that has been modified to disperse the nanoantennas. The nanoantennas can also be discretely dispersed from the air using an airplane or remotely-controlled flying apparatus. Nanoantennas can even be seeded by individuals using hand-held dispersal systems.

To efficiently backtrack the movements of a person, vehicle, or object, each road within a given location can be seeded with a unique nanoantenna, such as a nanoantenna that is functionalized with identifiable nucleic acid. As the vehicle moves through the location it picks up nanoantennas from each road it traverses. This system can be scaled up or scaled down to suit the needs of the seeder. For example, rather than seeding individual roads the seeder can use the nanoantennas to label large regions of land to backtrack large-scale movements. Alternatively, the seeder can scale down the method by seeding individual homes or buildings to identify individuals or objects that have entered those buildings.

In step 540 of FIG. 5, an item is examined for the presence of seeded nanoantennas, including using one or more of the methods/devices/systems described above, and depicted in FIG. 3. The detection process can be automated. An individual or object of interest can be forced to travel through a scanning point containing excitation equipment and emission detection equipment. As the individual or object of interest travels through the scanning point, the equipment scans for emitted photons of a certain wavelength. When the emitted photons are detected, a computer at the scanning point automatically alerts a remotely-located entity that subsequent analysis is necessary.

Once an object of interest is identified, the object can be examined for seeded nanoantennas using any mechanism designed to pick up nanoantennas from the surfaces of the object. In one embodiment, the nucleic acids attached to the identified nanoantennas taken from the exterior of an object are analyzed using any method that determines the exact order of nucleotide bases. There are currently a number of different commonly-used sequencing techniques including but not limited to dye-terminator sequencing, parallel sequencing, and sequencing by ligation. Sequencing machines allow automated sequencing and can be run 24 hours a day. If PCR techniques are used, the appropriate primers are chosen based upon the types of nucleic acid and/or tags known to be in the location of interest.

In addition to the traditional sequencing techniques described above, real-time PCR and sequencing by hybridization techniques allow rapid detection of target nucleic acids. According to the real-time PCR technique, the extracted nucleic acid is placed into a well or tube that has been pre-loaded with all reagents necessary for a PCR reaction as well as a sequence-specific, nucleotide-based, fluorescently-labeled probe. As the extracted nucleic acid is amplified, the polymerase degrades the probe and releases the fluorescent reporter. The reporter immediately fluoresces and alerts the system to the presence of a nucleotide. Under the sequencing by hybridization technique, the extracted nucleic acid is labeled with a fluorescent marker and is hybridized to a DNA microarray that contains the complementary nucleotide sequence from known seeded nucleic acid. If the extracted nucleic acid hybridizes to any of the complementary nucleic acid, the fluorescent signal alerts the system to the presence of a target nucleic acid. Since both methods of analysis avoid additional analysis and require relatively inexpensive analytical equipment, they promote faster and more affordable generation of data.

There are many other methods of characterization of the nucleic acid. For example, the nucleic acid can be detected using any molecular technique known to be suitable or adaptable for nucleic acid quantification or qualification, including but not limited to qPCR, high resolution melt ("HRM"), mass spectrometry, direct sequencing, strand displacement, and microarrays, among many others.

To characterize the identified nanoantennas and/or nucleic acid, the identified nanoantennas and/or the sequences obtained from the identified nucleic acid are compared to a database of nanoantennas and/or sequences at step 550 of the method depicted in FIG. 5. To efficiently determine the point of origin or recent travel history of an object, individuals analyzing in the field will need access or information about the nanoantennas dispersed by the seeders. A database of seeded nanoantennas will require maximum security measures to avoid improper access and manipulation, including access protection measures such as passwords. Standard computer algorithms are used to find exact or approximate matches between a nanoantenna in the field and a nanoantenna in the database. Once such a match is found, the user can reasonably suspect that the object of interest has recently traveled through the location seeded by that nanoantenna. If the real-time PCR or sequencing by hybridization techniques is used, the identification of the seeded nanoantennas is quickly determined by equipment that scans the plate or microarray for fluorescent label.

Step 560 of FIG. 5 is an optional step which is only required if the user is attempting to backtrack the route taken by an object of interest or extrapolate the object's point of origin. According to some uses of the present invention, simply learning that a person or object has traveled through a particular location is sufficient information. For other uses, it is necessary to analyze multiple nanoantennas. To extrapolate a route taken or a point of origin, the seeded nanoantenna location information obtained by analyzing the surfaces of the object is fed into a computer algorithm that quickly plots every potential route that the object has traveled based upon the possible combinations of nanoantenna locations. A similar algorithm can be used to extrapolate a point of origin based upon the identified nanoantenna locations.

Example 5

Upconverting Taggant

According to another embodiment is an exemplary process for creating a suitable upconverting taggant, which can be used for, for example, tagging, tracking, and/or locating, among many other uses. According to this embodiment, an upconverter is functionalized to a taggant.

Figure 6:
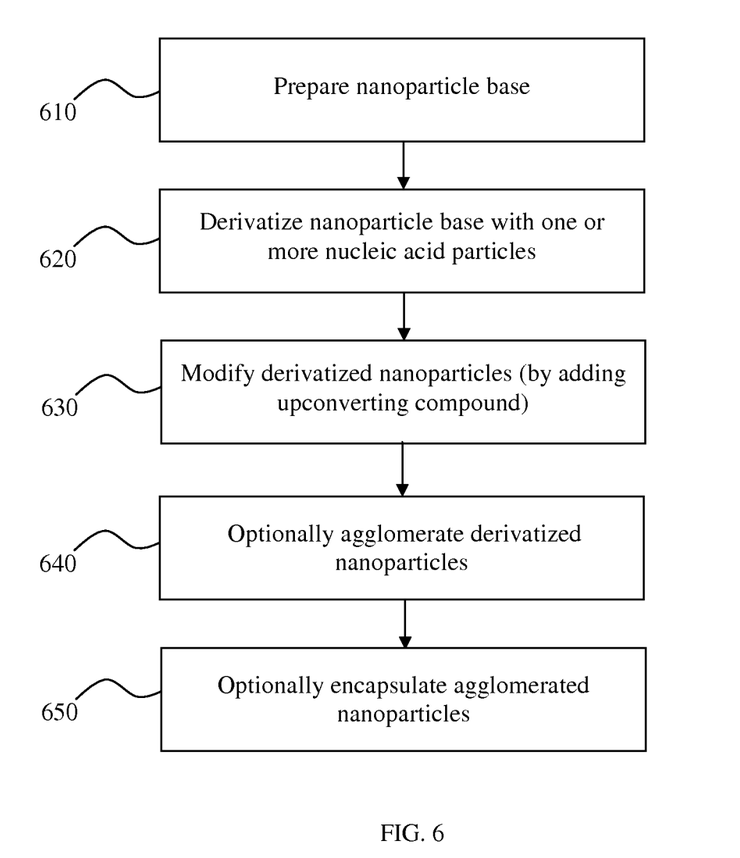
FIG. 6 is a flowchart of a process for creating a nanoparticle tag with an upconverting element in accordance with an embodiment.

According to one method, as an initial step 610, a nanometer-sized particle platform is prepared for attachment to one or more nucleic acid molecule(s). This platform is any compound that can be attached to nucleic acid without unintentionally degrading or altering the nucleic acid sequence. For example, the platform can be a lightweight, durable, non-water soluble, and chemically inert structure composed of silica or polystyrene. Additionally, the nanoparticle platform could be composed of a compound that does not inhibit any downstream analysis of the nucleic acid molecules, including tag detection or polymerase chain reaction ("PCR"), among other things.

At step 620, the nucleic acid molecule is attached to the prepared nanoparticle platform. The nucleic acid can be any natural or artificial nucleic acid, including but not limited to deoxyribonucleotides, ribonucleotides, oligonucleotides, nucleic acid analogs, and similar molecules that are either artificial or are otherwise found in nature, as well as combinations of any or all of the above. The nucleic acids can range from a very short sequence to a complete genome, for example. The nucleic acid molecules are optimally attached to the nanoparticle to facilitate later analysis. In a preferred embodiment, a chemical linker is used to connect the nucleic acid to the nanoparticle platform. This chemical linker must keep the nucleic acid securely tethered to the nanoparticle while avoiding inhibition of the detection or analysis of the tag and nucleic acid. Although the chemical linker can be chosen to provide a permanent covalent link between the nucleic acid and the nanoparticle platform, it could also be a compound that quickly and efficiently releases the nucleic acid at a certain temperature or after exposure to a release compound.

The nucleic acid molecule can also be designed to promote analysis. For example, to avoid steric hindrance or unwanted intermolecular interactions, the molecule can include nucleotide spacers between the chemical linker or nanoparticle base and the information-coding segment of the nucleotide sequence. Spacing between 5 and 15 bases has been optimal for current applications, although this may vary as new applications are considered.

The concentration of nucleic acid molecules on the nanoparticle platform is also an important factor in downstream analysis. If the molecules are too concentrated, steric hindrance prevents the primer and polymerase from efficiently binding the proper segments of the nucleic acid molecules. If the molecules are too sparse, the PCR signal will be diminished and can result in false negatives. In a preferred embodiment, a concentration of about $3 \times 10^{10}$ nucleic acid molecules per square centimeter is the optimal concentration for robust PCR signal.

At step 630, which can occur at the position shown in the flowchart or before or after any other step after derivatization of the nanoparticles, the derivatized nanoparticles can optionally be modified for any purpose, use, or design. The tag can also be modified with other compounds to provide additional desired characteristics including but not limited to color, luminescence, or protection against ultraviolet radiation.

According to one embodiment, the tag is modified with an emitting component that upconverts a wavelength through an anti-stokes mechanism. Anti-stokes upconverters are known in the art, and can include, but are not limited to, components including one or more various lanthanides, actinides, and transition metals, including Pr, Nd, Gd, Dy, Ho, Er, Tm, U, and Am, among many others. An anti-stokes upconverter can be an ion-doped crystal, doped with one or more of the ions described above or known in the art. For example, $LaCl_3:U^{3+}$, $NaYF_4:Yb^{3+}$, and $Y_2BaZnO_5$ or $Gd_2BaZnO_5$ doped with lanthanide ions such as $Yb^{3+}$, $Er^{3+}$, $Ho^{3+}$ and $Tm^{3+}$, and just a few examples of ion-doped crystals that can be used as upconverters. Many others are known in the art. The upconverting component can be functionalized to the tag using one of the methods or systems described herein, or can be added, combined, or attached to the tag using mechanisms known in the art for adding, combining, or attaching.

According to another embodiment, the upconverter-labeled tag is further modified by co-doping with a plasmonic enhancer such as Ag, or by using a core-shell approach. This, among many other mechanisms, can be used to enhance the energy transfer and result in a more efficient system. For example, the tag can comprise arrayed nanochannels that have one or more fluorophores which can capture light and have very limited molecular movement, making the energy transfer efficient. According to another embodiment, the fluorophores are bound to, for example, zeolite crystals and/or nanotubes to act as conductors, although other configurations are possible depending upon the design of the system and the needs of the designers and/or users. Other carries which restrict the molecular movement of the light acceptor are also possible. The coupling effect is further enhanced by the use of a silver base layer or other noble metal (including but not limited to ruthenium, rhodium, palladium, osmium, iridium, platinum, and gold) to act as a plasmon conductor and to achieve metal enhanced fluorescence.

At step 540 of the exemplary method, the nucleic acid-derivatized nanoparticles are optionally agglomerated. Agglomeration protects the nucleic acid molecules from degradation and facilitates encapsulation. To agglomerate the particles to the desired size range, the nanoparticles are vacuum dried, milled, and sieved.

Compounds might be used or incorporated into the tag to promote disagglomeration of the agglomerates prior to PCR analysis. These compounds might be bovine serum albumin, salmon sperm DNA, carbohydrates, polyvinyl alcohol, fructose, or chitosan, among others. With more nucleic acid exposed during dissolution, subsequent analysis will be faster and more sensitive.

After the nanoparticles are agglomerated, the agglomerates are optionally encapsulated at step 650. The encapsulant protects the nucleic acid from degradation by ultraviolet light, hydrolysis, enzymatic digestions, chemical degradation, or any other means. Additionally, the encapsulant can be designed such that it does not hinder analysis of the nucleic acid molecules. For example, the encapsulant should not contain any compounds that would inhibit or prevent a PCR reaction, although efficient removal of the encapsulant before PCR analysis would eliminate this requirement. Additionally, the encapsulant should enhance the ability of the tag to discretely attach to people and objects. If covertness is required, the encapsulant can be designed to deter detection.

The encapsulating layer can also be designed with surface moieties added to the inner or outer surfaces of the encapsulant or incorporated into the encapsulant material. The moieties are designed to facilitate a particular use of the nucleic acid tag. For example, the moiety can be hydrophobic to enable stickiness or contain antibodies designed for specific targeting. The molecular interactions between the moiety and a target compound can range from simple electrostatic interactions to antibody-antigen recognition. The moiety can also promote detection of the nucleic acid tag.

To protect the nucleic acid from degradation, the encapsulating layer can be coated with or include another functional layer of material. For example, the encapsulant can be coated with or include a non-water-soluble compound to prevent access to water or similar molecules.

Figure 7:
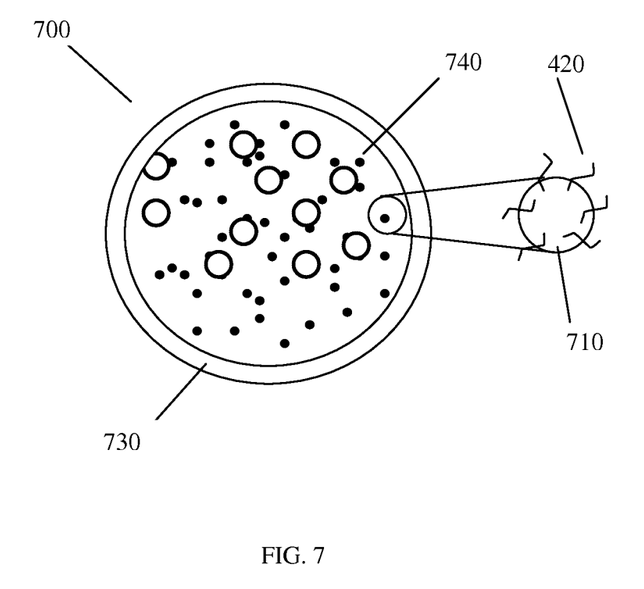
FIG. 7 is a side view of an encapsulated nucleotide tag complex with an upconverting element trapped inside the tag by the encapsulant layer in accordance with an embodiment of the present invention.

FIG. 7 is a side view of an embodiment of a tag structure. Tag 700 is composed of nucleotide-support platform 710 derivatized with nucleic acid 720 and surrounded by encapsulant 730. Tag 700 can contain thousands, millions, or even billions of nucleotide-derivatized nanoparticles within the encapsulant layer. In this example, upconverting element 740 is separate from nucleotide-support platform 710 and encapsulant 730 but is trapped within the interior of tag 700. Other methods of incorporating upconverting element 740 are possible. For example, upconverting element 740 is incorporated into the encapsulant surrounding the tag, or it can form a portion of the structure or base that the nucleic acid is bound to, or it can form a layer on the exterior surface of the encapsulant, or it can be incorporated into the exterior layer of the tag itself, among other methods.

Although the present invention has been described in connection with a preferred embodiment, it should be understood that modifications, alterations, and additions can be made to the invention without departing from the scope of the invention as defined by the claims.

What is claimed is:

1. A method for determining whether an item has moved through a geographic location using a nanoantenna, the method comprising:
   providing a nanoantenna, the nanoantenna comprising: (i) optical wiring comprising a plurality of wires each comprising a plurality of nanochannels, said nanochannels adapted to receive electromagnetic radiation of a first wavelength; and (ii) an upconverting fluorescent material in communication with said plurality of nanochannels, wherein when the nanoantenna is exposed to said electromagnetic radiation of said first wavelength, the upconverting fluorescent material emits electromagnetic radiation of a second wavelength, said second wavelength being shorter than said first wavelength;
   seeding the geographic location with the nanoantenna;
   allowing time for the item to move through the seeded geographic location, wherein the item will be seeded with the nanoantenna;
   examining the item for the presence of the nanoantenna, comprising the steps of:
      providing a nanoantenna detection array, the detection array comprising a large diameter telescope having a solar-blind avalanche photodiode, wherein the detection array is positioned a first distance from the item such that the item is within a focal point of the telescope;
      orienting the detection array toward the item to obtain light reflected from or emitted by the item; and
      detecting, with the detection array, a UV-C emission from the first nanoantenna, if the item has moved through the seeded geographic location;
   determining that the item has moved through the seeded geographic location if the nanoantenna is present on the item.

2. The method of claim 1, wherein a plurality of nucleic acid molecules are attached to said nanoantenna.

3. The method of claim 2, wherein information is encrypted within at least one of said plurality of nucleic acid molecules.

4. The method of claim 1, further comprising the step of: analyzing at least a portion of the sequence of at least one of said plurality of nucleic acid molecules.

5. A method for determining the travel history of an item, the method comprising:
   providing a first nanoantenna, the first nanoantenna comprising: (i) optical wiring comprising a plurality of wires each comprising a plurality of nanochannels, said nanochannels adapted to receive electromagnetic radiation of a first wavelength; and (ii) a first upconverting fluorescent material in communication with said plurality of nanochannels, wherein when the first nanoantenna is exposed to said electromagnetic radiation of said first wavelength, the first upconverting fluorescent material emits electromagnetic radiation of a second wavelength, said second wavelength being shorter than said first wavelength;
   providing a second nanoantenna, the second nanoantenna comprising: (i) optical wiring comprising a plurality of wires each comprising a plurality of nanochannels, said nanochannels adapted to receive electromagnetic radiation of a third wavelength; and (ii) a second upconverting fluorescent material in communication with said plurality of nanochannels, wherein when the second nanoantenna is exposed to said electromagnetic radiation of said first wavelength, the second upconverting fluorescent material emits electromagnetic radiation of a fourth wavelength, said fourth wavelength being shorter than said third wavelength;
   seeding each of two or more geographic locations with said nanoantennas, wherein each geographic location is seeded with a unique nanoantenna;
   allowing time for the item to move through one or more of the seeded geographic locations, wherein the item will be seeded with one or more nanoantennas;
   examining said item for the presence of one or more nanoantennas, comprising the steps of:
      providing a nanoantenna detection array, the detection array comprising a large diameter telescope having a solar-blind avalanche photodiode, wherein the detection array is positioned a first distance from the item such that the item is within a focal point of the telescope;
      orienting the detection array toward the item to obtain light reflected from or emitted by the item; and
      detecting, with the detection array, a UV-C emission from at least one of the one or more nanoantennas on said item, wherein if one or more of the seeded nanoantennas are present on the item then the item has moved through the seeded geographic location associated with the detected one or more of seeded nanoantennas;

identifying one or more geographic locations associated with each nanoantenna detected on said item; and determining the travel history of the item based on the identified one or more geographic locations.

6. The method of claim 5, wherein said first wavelength and said third wavelength are the same.

7. The method of claim 5, the method further comprising the step of:

extrapolating the point of origin of said item.

8. A method for determining the travel history of an item, the method comprising:

providing a plurality of nanoantennas, each nanoantenna comprising: (i) optical wiring comprising a plurality of wires each comprising a plurality of nanochannels, said nanochannels adapted to receive electromagnetic radiation of a first wavelength; (ii) an upconverting fluorescent material in communication with said plurality of nanochannels, wherein when the nanoantenna is exposed to said electromagnetic radiation of said first wavelength, the upconverting fluorescent material emits electromagnetic radiation of a second wavelength, said second wavelength being shorter than said first wavelength, and further wherein a plurality of nucleic acid molecules comprising a first nucleic acid sequence are attached to a first subset of said plurality of nanoantennas, and further wherein a plurality of nucleic acid molecules comprising a second nucleic acid sequence are attached to a second subset of said plurality of nanoantennas;

seeding at least two or more geographic locations with said nanoantennas, wherein the first geographic location is seeded with said first subset of nanoantennas, and the second geographic location is seeded with said second subset of nanoantennas;

allowing time for the item to move through one or more of the seeded geographic locations, wherein the item will be seeded with one or more nanoantennas;

examining said item for the presence of one or more nanoantennas, comprising the steps of:

providing a nanoantenna detection array, the detection array comprising a large diameter telescope having a solar-blind avalanche photodiode, wherein the detection array is positioned a first distance from the item such that the item is within a focal point of the telescope;

orienting the detection array toward the item to obtain light reflected from or emitted by the item; and detecting, with the detection array, a UV-C emission from at least one of the one or more nanoantennas on said item, wherein if one or more of the seeded nanoantennas are present on the item then the item has moved through the seeded geographic location associated with the detected one or more of seeded nanoantennas;

identifying one or more geographic locations associated with each nanoantenna detected on said item; and determining the travel history of the item based on the identified one or more geographic locations.

9. The method of claim 8, wherein information is encrypted within at least one of said nucleic acid molecules.

10. The method of claim 8, further comprising the step of: analyzing at least a portion of the sequence of at least one of said nucleic acid molecules.

\* \* \* \* \*